United States Patent
Schulteis

(10) Patent No.: US 6,518,221 B1
(45) Date of Patent: Feb. 11, 2003

(54) PLANT GROWTH REGULATOR AND METHOD FOR USING SAME

(75) Inventor: David T. Schulteis, Fresno, CA (US)

(73) Assignee: Wilbur-Ellis Company, San Francisco, CA (US)

(*) Notice: Subject to any disclaimer, the term of this patent is extended or adjusted under 35 U.S.C. 154(b) by 0 days.

(21) Appl. No.: 10/194,724

(22) Filed: Jul. 11, 2002

(51) Int. Cl.$^7$ ............ A01N 33/12; A01N 59/06; A01N 59/16
(52) U.S. Cl. ............ 504/121; 504/118; 504/120; 504/123; 504/148
(58) Field of Search ............ 504/121, 118, 504/120, 123, 148, 163, 173

(56) References Cited

U.S. PATENT DOCUMENTS

| | | | | |
|---|---|---|---|---|
| 3,557,214 A | * | 1/1971 | Koenig et al. | 564/296 |
| 3,771,989 A | * | 11/1973 | Pera et al. | 504/160 |
| 4,439,224 A | * | 3/1984 | Schulteis | 504/130 |
| 4,637,828 A | * | 1/1987 | Schulze et al. | 504/139 |
| 4,799,950 A | * | 1/1989 | Suzuki et al. | 504/140 |
| 5,015,283 A | * | 5/1991 | Miyazawa et al. | 504/130 |
| 6,376,425 B1 | * | 4/2002 | Kober et al. | 504/116.1 |

FOREIGN PATENT DOCUMENTS

GB 1092138 * 11/1967

OTHER PUBLICATIONS

Farm Chemicals Handbook '98, Meister Publishing Co., Willoughby, Ohio, vol. 84, 1988, pp. C 86 and C415.*

* cited by examiner

*Primary Examiner*—John Pak
(74) *Attorney, Agent, or Firm*—R. Michael West; Boutin, Dentino, Gibson, Di Giusto, Hodell & West

(57) ABSTRACT

A composition for regulating the growth of plants in which an effective amount of chlorocholine chloride, poly [oxyethylene(dimethyliminio)ethylene(dimethyliminio) ethylene]dichloride, and choline chloride, is diluted in an inert carrier. The inert carrier may be water, a solvent, or a surfactant. The composition with the diluent forms a liquid solution, which is sprayed on the foliage of subject plants prior to harvest. At least one inorganic salt may be added to the composition to enhance the efficacy of the liquid solution. A first formulation of the solution, preferably including the inorganic salt additive, may be applied early in the plant's development to discourage rank growth without inducing Cut-Out. A second formulation of the solution, having no inorganic salt but including a greater amount of chlorocholine chloride, may be applied late in the plant's development, to induce Cut-Out.

20 Claims, 2 Drawing Sheets

PLANT GROWTH REGULATOR AND METHOD FOR USING SAME

BACKGROUND OF THE INVENTIION

1. Field of the Invention

The invention relates generally to chemical compositions and methods for using same, for regulating the growth of plants. More particularly the invention pertains to a liquid solution formed from a mixture of chlorocholine chloride, poly[oxyethylene(dimethyliminioethylene(dimethyliminio) ethylene]dichloride, choline chloride, and an inert carrier, which is spray applied to crop plants at selective times and in selective concentrations to improve crop yield.

2. Description of the Prior Art

Plant growth regulators are well known in the prior art. For example, in U.S. Pat. No. 3,905,798, the application of salts of cyclic nitrogenous compounds to cotton plants for controlling their growth, is described. German Patent 28 15 443 teaches growth regulation of cotton plants through the aerial application of N, N-dimethylpiperidinium chloride, another cyclic nitrogenous compound. Yet another compound, designed to regulate the growth of cotton plants, is described in U.S. Pat. No. 4,439,224. This compound is made from a mixture of N,N-dimethylpiperidinium chloride (hereinafter "PIX"), and poly[oxyethylene(dimethyliminio) ethylene(dimethyliminio)ethylene] chloride.

When cyclic nitrogenous compounds are applied to cotton plants under stress, it is common for the plants to be shocked into "Cut-Out". This term is recognized in the industry as describing the condition of a cotton plant when it stops all vegetative and reproductive growth. If this condition is induced by chemical treatment or occurs naturally, at some point early in the season prior to the plant's normal physiological timing, dramatic crop yield reductions will occur.

The non-cyclic nitrogenous salt, 2-chloroethyltrimethylammonium chloride, also known more commonly as Chlorocholine Chloride and sold under the trademark CYCOCEL, has also been used to regulate the growth of cotton and cereal plants. In fact, Chlorocholine Chloride ("CCC") is well established as the standard plant growth control product in cereal production. The cyclic nitrogenous compound PIX is disfavored to treat cereal plants, as it is not as effective to control growth in such plants.

However, with respect to cotton plants, Chlorocholine Chloride is not accepted as the best commercial product. It is recognized that CCC produces unpredictable results and exhibits a high risk of reducing the crop yield of cotton plants, when compared to PIX. With cotton plants, Chlorocholine Chloride tends to induce the above-described Cut-Out problem. For example, the commercial product STABILIN, containing 38.4% chlorocholine chloride, is registered by the government in Greece for use on cotton to control plant growth. The recommended application rate for STABILIN is 40 grams per hectare, applied twice, with a first application made 45 days after germination followed by a second application 14 days later. This high rate of CCC application, totaling 80 grams per hectare, provides controlled growth of the cotton plant but is accompanied by an undesirable decrease in crop yield.

Another generally recognized recommendation in the industry is to apply Chlorocholine Chloride on cotton at a rate of 400 to 2000 grams per hectare, about 75 to 90 days after seeding. These rates for CCC application are significantly higher than the suggested use rates of 25 to 50 grams per hectare, for the cyclic nitrogenous product, N, N-dimethylpiperidinium chloride. Unfortunately, the high application rates of CCC increase the probability of inducing Cut-Out and attendant crop yield reduction.

SUMMARY OF THE INVENTION

A plant growth regulator is disclosed which is particularly effective for use with cotton plants. The plant growth regulator is a composition, preferably in the form of a liquid solution, made by mixing together chlorocholine chloride, poly[oxyethylene(dimethyliminio)ethylene (dimethyliminio)ethylene]dichloride, choline chloride, and an inert carrier, such as water.

Selected inorganic salts are preferably added to the liquid solution, to improve its performance as a growth regulator. For example, when calcium and zinc ions are added to the solution, the harshness of the CCC is buffered and crop retention by the plant is improved. Calcium ions increase the efficacy of CCC, allowing lower application rates than would otherwise be required to control plant growth effectively. Zinc ions promote the synthesis of auxin, and enhance the plant's ability to maintain fruit set and boll retention.

In a first application, the liquid solution is spray-applied to the foliage of young subject plants, well prior to crop harvest. The timing of the application and the concentration of the active ingredients used are such that undesirable rank growth is inhibited, while fruit-setting and fruit growth are encouraged. Cut-Out of the plants is avoided, as the composition of the solution uses much less CCC, yet remains efficacious.

A second application of the liquid solution may also be made, just prior to harvest. The formulation of the solution used in this second application is different. The inorganic salts which are preferred for use in the first application, are not included. This modification is made as the addition of new fruit to the plants is undesirable just before harvest. In addition, a more concentrated form of the solution is used to induce Cut-Out of the plants. Accordingly, at this stage in the plant's development, the formulation of the solution is tailored to accelerate plant maturity and condition the plants for defoliation or desiccation.

DETAILED DESCRIPTION OF THE PREFERRED EMBODIMENT

The plant growth regulator of the present invention is a composition which includes chlorocholine chloride as its active ingredient. Chlorocholine chloride is marketed under a variety of trademarks including STABALIN by Nufarm Limited, of Laverton, North Victoria, Australia, CYCOCEL by American Cyanamid Company of Parsippany, N.J., and CCC by BASF Corporation, having Regional Headquarters in Research Triangle Park, N.C. For the sake of clarity, the term CCC will be used herein, to refer to chlorocholine chloride. However, it should be understood that in the Examples 1–3 which follow, all references to chlorocholine chloride pertain to an undiluted, non-commercial form of that water soluble compound. This proviso also applies to references made in the Examples to other chemical compounds, which also use an undiluted form of the respective compounds, not the diluted commercial forms.

The second chemical component of the plant growth regulator is poly[oxyethylene(dimethyliminio)ethylene (dimethyliminio)ethylene]dichloride, commercially marketed under the trademark WSCP by Buckman Laboratories of Memphis, Tenn. The commercial product WSCP is a water-soluble composition containing on a weight basis 60% poly[oxyethylene(dimethyliminio)ethylene-(dimethyliminio)ethylene]dichloride and 40% inert ingredients. It should also be noted that WSCP can be prepared by following the method described in U.S. Pat. No. 3,771,989, the teachings of which are hereby expressly incorporated by reference.

The third chemical component of the plant growth regulator is choline chloride, marketed by the Trouw Nutrition USA, of Highland, Ill., under the trademark CC. CC is a Vitamin B additive, commercially sold as an animal feed supplement. It is noteworthy that when a plant treated with CCC metabolizes the CCC, the CCC degrades into CC.

Water is the preferred inert carrier or diluent for the plant growth regulator, as CCC, WSCP, and CC are all water soluble chemicals. In addition, water is a readily available and economical carrier, and readily adaptable for use with existing chemical spray application technology. A solvent or a surfactant may also be used in conjunction with the water to increase the penetration of the plant growth regulator into the treated plant foliage. Alternatively, the solvent or surfactant may be used as a substitute for the water as the inert carrier.

Figure 1:
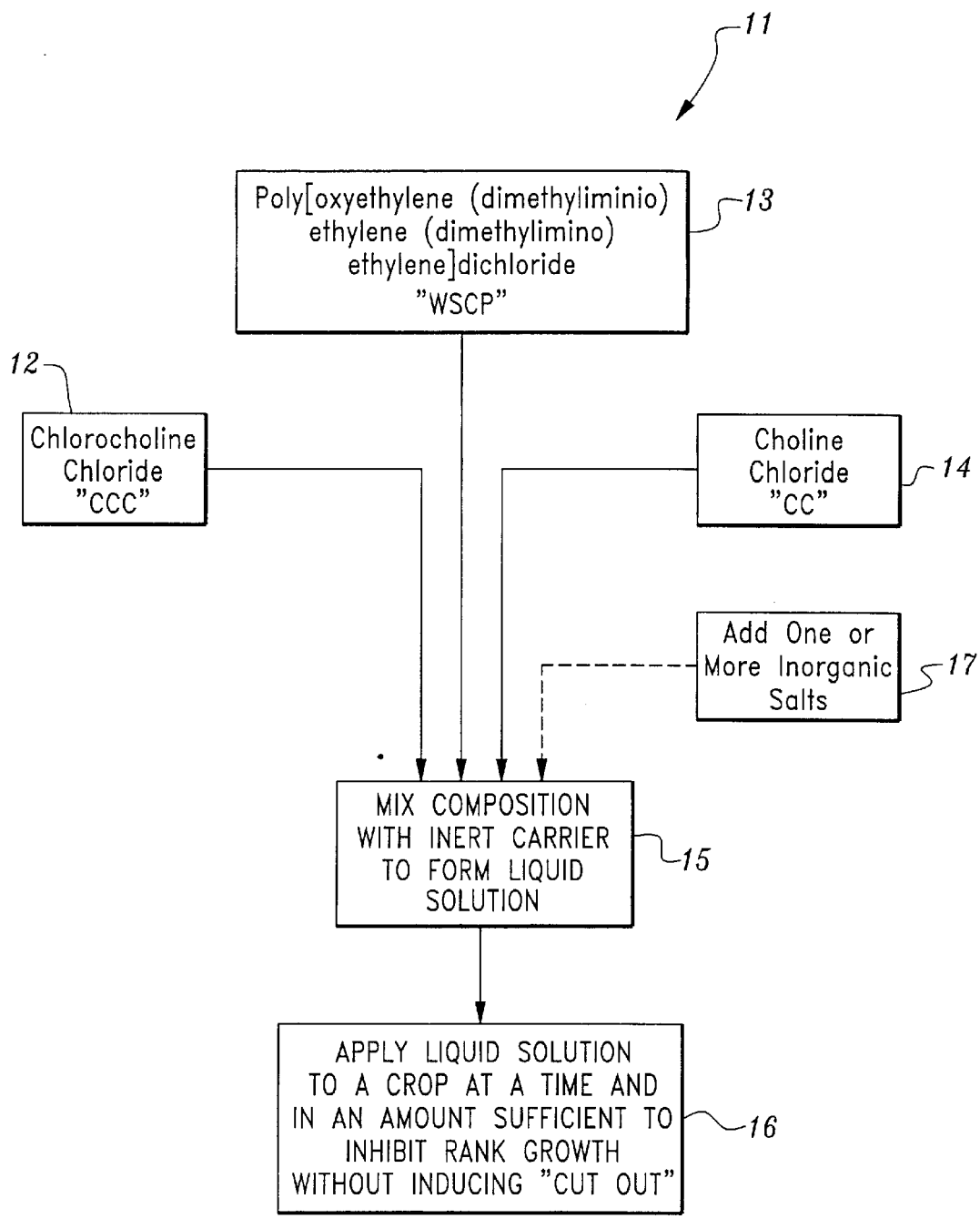
FIG. 1 is a diagrammatic representation of the preferred process for making and applying the composition of the present invention in a first application to plants; and, FIG. 2 is a diagrammatic representation of the preferred process for making and applying the composition of the present invention in a second application to plants.

A method 11 for mixing and applying the liquid solution of the present invention is shown in FIG. 1. A composition of CCC 12, WSCP 13, and CC 14, is mixed with an inert carrier in step 15, to form a first formulation of the liquid solution. The amount of inert carrier used as a diluent determines the concentration of the plant growth regulator in the liquid solution. The concentration of the plant growth regulator, and the resultant amount of the regulator ultimately applied per unit of land, depends upon the desired result for that crop. In addition, the timing and number of applications of the plant growth regulator are additional factors which must be taken into consideration for its effective use.

For example, in a first application of the plant growth regulator, the objectives are to inhibit undesirable rank growth and to promote fruit-setting and fruit growth. To effect this goal, the liquid solution of the plant growth regulator has a concentration such that when it is spray-applied to the foliage of the subject crop, about 0.5 to 10 grams of the active ingredients are applied per hectare. Occasionally, application rates as high as 20 grams, or so, of active ingredient per hectare may be necessary where certain plant varieties are subject to environmental conditions which promote excessive vegetative growth.

The optimal application rate depends upon a number of factors such as plant variety, physiological age of the plant, plant density, temperature, humidity, soil characteristics, and efficiency of the application. It is well known that as the physiological age of the plant advances, greater amounts of the active ingredients must be used to control rank growth. Also, if a plant is under stress, induced by lack of water or high temperatures, a lesser amount of active ingredient will be effective for the desired result. Persons of ordinary skill in the art recognize these factors and the part they play in the required application rates to achieve the desired result.

This application is made early in the growing season, about ten to twenty weeks before harvest. Thus, the timing of this first application is made at an early stage of the plant's development. Moreover, the first application to the plant is made in an amount effective to inhibit the rank growth of the plant, without inducing plant Cut-Out. This first spray-application of the liquid solution is represented by step 16 in FIG. 1. One of the advantages of the liquid solution of the present invention is that it can be applied using well known spraying methods and readily available spraying apparatus. No special treatment method or devices are necessary to apply the liquid solution effectively to a crop field.

It is also preferred, although not necessary, to add one or more inorganic salts 17 to the liquid solution, when the composition and the inert carrier are mixed in step 15. This additional procedure is represented by a broken line extending between salts 17 and step 15, in FIG. 1. The inorganic salt or salts used are selected from the group consisting of calcium nitrate, calcium chloride, zinc nitrate, zinc chloride, zinc sulfate, ammonium nitrate, calcium ammonium nitrate, manganese nitrate, manganese sulfate, magnesium nitrate, and magnesium sulfate.

Calcium is a well-known critical component of the calcium-calmodulin enzyme complex which is responsible for initiating the internal physiological processes inside plant cells. As a consequence, when a substance is applied to a plant that is intended to cause a plant growth regulatory effect, sufficient calcium must be available inside the cell of the plant to combine with calmodulin to form the calcium-calmodulin complex. If calcium is lacking in the plant cells, the efficiency of the applied plant growth regulator chemical is greatly reduced. Thus, one of the preferred inorganic salts to add to the liquid solution is calcium, in the form of calcium nitrate or calcium chloride.

Zinc is also a very important element associated with the growth of a plant. Zinc is a component of a metallic co-enzyme complex that converts the amino acid tryptothane into auxin, also known as Indoleacetic Acid. Adequate levels of auxin are necessary to promote normal growth and to maintain fruit set and boll retention. If the level of auxin in a cotton plant drops below a threshold level, an abscission process starts that results in the shedding of bolls. This phenomena is especially important in the early setting of bolls in the life of a cotton plant. It is the first bolls formed on the cotton plant which produce the bulk of the crop. However, the application of plant growth regulators when the first bolls are formed presents the greatest risk for inducing the abscission process. Adding zinc to the liquid solution, in the form of zinc nitrate, zinc chloride, or zinc sulfate provides supplemental zinc ions to the plant to ensure that adequate auxin is produced and boll abscission is avoided.

Figure 2:
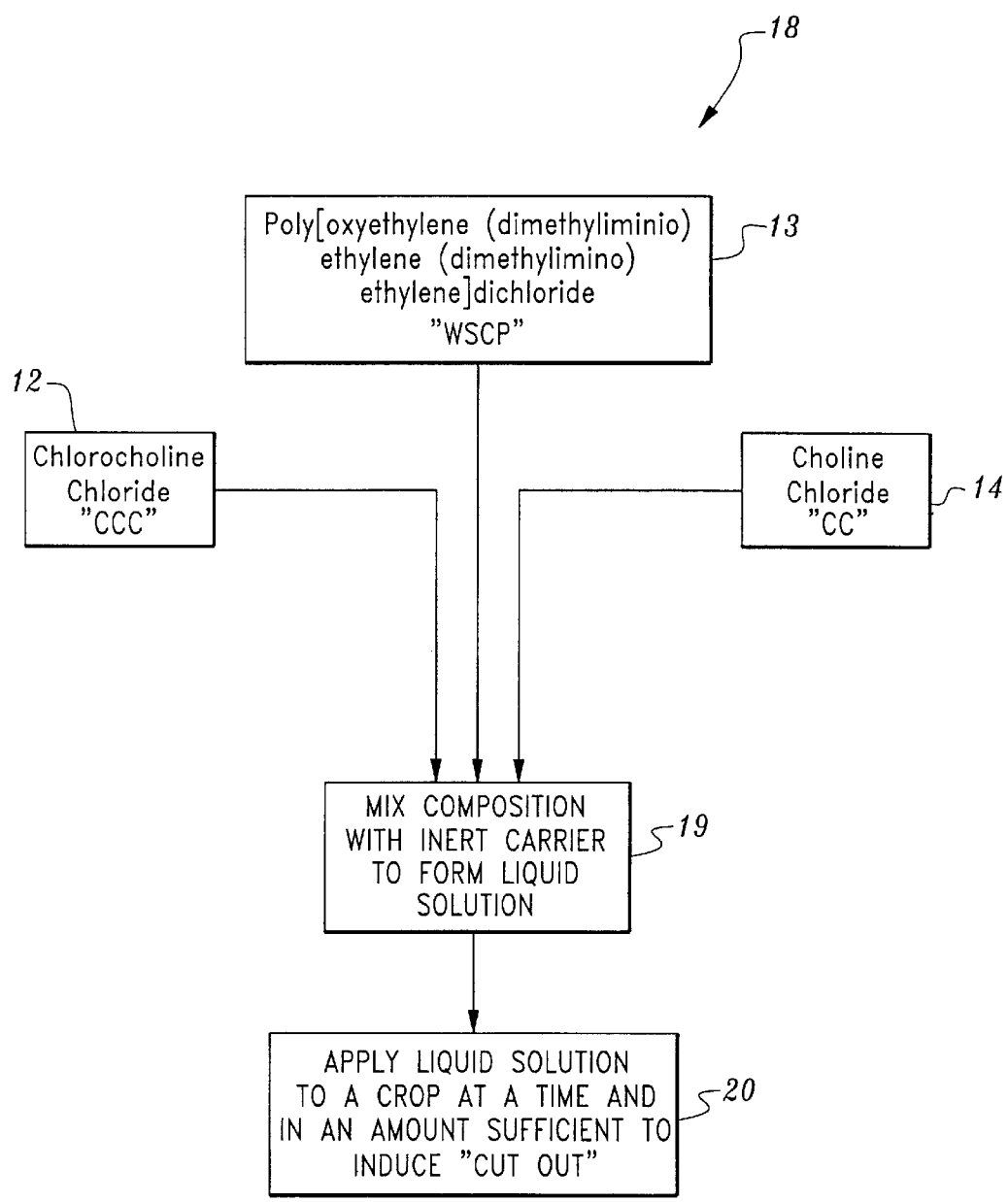

Turning now to FIG. 2, a method 18 for mixing and applying a second formulation of the liquid solution of the present invention is shown. This second formulation may be used for a second application of the plant growth regulator, made just prior to harvest. The formulation of the liquid solution used in this second application is different. The inorganic salts which are preferred for use in the first application, are not included. This modification is made as the addition of new fruit to the plants is undesirable just before harvest. In addition, a more concentrated form of the solution is used to induce Cut-Out of the plants. Accordingly, at this stage in the plant's development, the formulation of the solution is tailored to accelerate plant maturity and to condition the plants for defoliation or desiccation.

The second application of the plant growth regulator is preferably made about 2–9 weeks before harvest. The timing of this second application, the lack of inorganic salts in the second formulation, and the greater amount of plant regulating chemicals applied in the second application, are all calculated to induce plant "Cut-Out". Those of ordinary skill in the art will recognize that a significant change in any one of these factors alone could affect the speed and degree of "Cut-Out" induced in the plant. In addition, environmental factors such as humidity, soil condition, temperature, and length of the day, also play a part in the rate and extent of the induced "Cut-Out". Notwithstanding these recognized variables, the second formulation of the liquid solution is applied at a time and in an amount sufficient to induce "Cut-Out", so the crop can more quickly and efficiently be harvested.

So that the practical application and the results of using the liquid solution of the present invention will more fully be understood and appreciated, the following examples are set forth. It should be understood, however, that these examples are merely illustrative, and the scope and content of the disclosed invention are not in any way limited by the specific conditions or details of formulations which follow.

EXAMPLE 1

A study was conducted on MAXXA cotton to determine the effects of Mepiquat Chloride and the combination of (CCC) chlormequat chloride/WSCP on plant growth and development. The results are presented in the following table:

| Chemical Treatment | Average Plant Height | Average Nodes | Average Vegetative Nodes | Average Fruiting Branches | Average Top 5 FPB* | Average Bottom 5 FPB* |
|---|---|---|---|---|---|---|
| 1. Mepiquat Chloride (10 gm/A) | 35.9" | 21.7 | 6.1 | 15.7 | 43.0 | 60.0 |
| 2. CCC + WSCP (2.5 gm/A) | 32.7" | 20.0 | 6.0 | 14.0 | 27.0 | 76.0 |
| 3. CCC + WSCP (5.0 gm/A) | 28.0" | 18.3 | 6.0 | 12.3 | 19.0 | 71.0 |
| 4. CHECK (Untreated) | 39.0" | 22.7 | 5.7 | 17.0 | 45.0 | 61.0 |

*FPB: First Position Bolls As A Percentage

In this example, the amount of WSCP used in each chemical treatment was constant, and the amount of CCC varied from 2.5 to 5.0 grams/acre. The corresponding ratios of WSCP and CCC were as follows: at the 2.5 gram/acre rate the ratio of WSCP to CCC was 30:1; at the 5.0 gram/acre rate the ratio of WSCP to CCC was 15:1. It should also be noted that 5.0% calcium and 1.25% zinc were also added to each of the mixtures.

The increase in Bottom 5 First Position Bolls is statistically significant as these bolls are the most productive and the key indicator of increased yield. In addition, the lower percentage figures of the Top 5 First Position Bolls indicate that the application of CCC and WSCP had a definite effect on advancing maturity of the plant. This is an important plant development for obtaining good defoliation.

These results demonstrate the effectiveness of the chemical combination of CCC and WSCP as a cotton plant growth regulator. Although CC (Choline Chloride) was not added to the CCC and WSCP formulations, Example 1 shows that the combination of CCC and WSCP alone can function as an effective plant growth regulator on cotton plants which is equal, if not superior, to Mepiquat Chloride. This result was unexpected.

EXAMPLE 2

A field study was conducted in the State of Mississippi on a Stoneville cotton variety, in which the physiological characteristics of plants treated with the plant growth regulator of the present invention (a mixture of CCC, WSCP, and CC), were compared to the characteristics of untreated plants, or "checks", and the characteristics of plants treated with PIX.

The formulation of the present invention used in Example 2 was as follows: the ratio of WSCP to CCC was reduced to 2.7:1, and the ratio of CC (Choline Chloride) to CCC was 0.6:1. Also added to the formulation was 5.0% calcium and 1.25% zinc.

The rate of PIX application was 10 grams per acre, applied once on July $8^{th}$ of the study year. The rate and timing of this application was consistent with the manufacturer's label recommendation. The rate of application of the plant growth regulator of the present invention was 2.5 grams per acre, applied once on June $28^{th}$ and again on July $18^{th}$. As with Example 1, the formulations of PIX used in Example 2, included 5.0% calcium and 1.25% zinc.

The physiological characteristics under study determine the effectiveness of the chemical products on fruit, or boll, set. The first fruiting position on a reproductive branch is the most important plant feature that affects expected plant yield. Consequently, the higher the percentage of fruit set at the first fruiting position the higher the fruit yield potential.

| Test Parameter | Untreated CHECK | PIX Treatment | Present Invention |
|---|---|---|---|
| First Fruiting Branch | 6 | 6 | 6 |
| Percentage Of First Fruiting Positions (Nodes 6–13) | 67.5% | 76.3% | 90.0% |
| Total Percentage Of Fruit Set (Nodes 6–13) | 56.7% | 65.0% | 79.2% |

The study reveals that there was a significant increase in the Percentage Of First Fruiting.Positions and in the Total Percentage Of Fruit Set, when the plant growth regulator of the present invention was used. In addition, an unexpected result of Example 2 was the realization that by adding CC to WSCP and CCC, much lower ratios of WSCP to CCC can be as effective. In other words, the combination of CCC, WSCP, and CC allowed much lower ratios of WSCP to CCC, while retaining the same efficacy as the formulation of Example 1 (WSCP and CCC).

EXAMPLE 3

Field trials were established in the country of Greece to determine the plant growth regulating effects of several products, including the chemical formulation of the present invention. The particular formulation of the present invention used in these trials, was as follows: 1.0 parts CCC; 2.7 parts WSCP; 0.6 parts CC; 27 parts Calcium; and, 6.75 parts Zinc (parts per weight). All of the chemical applications were applied at the same time, and there were three replications at each trial site. The results of those trials are presented in the following tables.

| Site | Treatment | Dose Rate | Plant Height |
|---|---|---|---|
| 1 | Untreated | N/A | 20.44 Cm |
|   | Invention | 5.0 gm/Ha | 11.56 Cm |
|   | Invention | 10.0 gm/Ha | 10.89 Cm |
|   | PIX | 20.0 gm/Ha | 10.00 Cm |
| 2 | Untreated | N/A | 68.22 Cm |
|   | Invention | 5.0 gm/Ha | 42.22 Cm |
|   | Invention | 10.0 gm/Ha | 31.00 Cm |
|   | PIX | 20.0 gm/Ha | 27.33 Cm |
| 3 | Untreated | N/A | 18.2 Cm |
|   | Invention | 5.0 gm/Ha | 8.56 Cm |
|   | Invention | 10.0 gm/Ha | 9.89 Cm |
|   | PIX | 20.0 gm/Ha | 7.78 Cm |

These results demonstrate the efficacy of the composition of the present invention to function as a cotton growth regulator. Example 3 confirmed the results of Example 2 in that unexpectedly lower ratios of WSCP to CCC, when combined with CC, were as effective as the higher ratio formulation made the subject of Example 1. And, since CC is much less expensive than WSCP, the formulation of CCC, WSCP, and CC which allows the much lower ratio of WSCP is desirable both from performance and cost considerations.

In addition The rates of application of the composition of the present invention are much lower than the currently registered chlormequat chloride CCC containing products. This low rate works as effectively as the label application rates of mepiquat chloride in controlling plant growth.

It will be appreciated, then, that I have disclosed a plant growth regulator preferably formulated from a mixture of chlorocholine chloride, poly[oxyethylene (dimethyliminioethylene-(dimethyliminio)ethylene] dichloride, choline chloride, and an inert carrier, which is spray applied one or more times to a crop, at selective times and in selective concentrations, to improve crop yield.

What is claimed is:

1. A composition for regulating the growth of plants consisting essentially of an effective amount of chlorocholine chloride, poly[oxyethylene(dimethyliminio)ethylene (dimethyliminio)ethylene]dichloride, choline chloride and optionally at least one inorganic salt, diluted in an inert carrier.

2. A composition as in claim 1 in which said chlorocholine chloride is present on a weight basis of about 1.0 parts, said poly[oxyethylene(dimethyliminio)ethylene (dimethyliminio)ethylene]dichloride is present on a weight basis of about 2.7 parts, and said choline chloride is present on a weight basis of about 0.6 parts.

3. A composition as in claim 2 in which said inorganic salt is selected from the group consisting of calcium nitrate, calcium chloride, zinc nitrate, zinc chloride, zinc sulfate, ammonium nitrate, calcium ammonium nitrate, manganese nitrate, manganese sulfate, magnesium nitrate, and magnesium sulfate.

4. A composition as in claim 1 in which said inert carrier is water.

5. A composition as in claim 1, wherein said at least one inorganic salt is present in the composition.

6. A composition as in claim 5 in which said inorganic salt is selected from the group consisting of calcium nitrate, calcium chloride, zinc nitrate, zinc chloride, zinc sulfate, ammonium nitrate, calcium ammonium nitrate, manganese nitrate, manganese sulfate, magnesium nitrate, and magnesium sulfate.

7. A method of regulating the growth of plants comprising the steps of:
   a. mixing a composition of chlorocholine chloride, poly[oxyethylene(dimethyliminio)ethylene (dimethyliminio)ethylene]dichloride, and choline chloride;
   b. diluting said composition in an inert carrier, producing a liquid solution; and,
   c. applying said liquid solution to the foliage of a plant, prior to the harvest of a crop therefrom, in an amount effective to inhibit the growth of the plant and to increase the crop yield thereof.

8. A method as in claim 7 in which said chlorocholine chloride is present on a weight basis of about one part, said poly[oxyethylene(dimethyliminio)ethylene (dimethyliminio)ethylene]dichloride is present on a weight basis of about three parts, and said choline chloride is present on a weight basis of about 1.5 parts.

9. A method as in claim 8, wherein said composition further includes at least one inorganic salt.

10. A method as in claim 9 in which said inorganic salt is selected from the group consisting of calcium nitrate, calcium chloride, zinc nitrate, zinc chloride, zinc sulfate, ammonium nitrate, calcium ammonium nitrate, manganese nitrate, manganese sulfate, magnesium nitrate, and magnesium sulfate.

11. A method as in claim 7 in which said inert carrier is water.

12. A method as in claim 7, wherein said composition further includes at least one inorganic salt.

13. A method as in claim 12 in which said plant nutrient is selected from the group consisting of calcium nitrate, calcium chloride, zinc nitrate, zinc chloride, zinc sulfate, ammonium nitrate, calcium ammonium nitrate, manganese nitrate, manganese sulfate, magnesium nitrate, and magnesium sulfate.

14. A method as in claim 7 in which said diluted composition is applied to the plant approximately two to twenty weeks prior to harvest.

15. A method as in claim 7 in which said effective amount is approximately 0.5 grams per hectare to approximately 20 grams per hectare.

16. A composition as in claim 8 in which said effective amount is approximately 0.5 grams per hectare to approximately 20 grams per hectare.

17. A method of regulating the growth of a plant comprising the steps of:
   a. mixing together chlorocholine chloride, poly[oxyethylene(dimethyliminio)ethylene (dimethyliminio)ethylene]dichloride, choline chloride, at least one inorganic salt, and an inert carrier, to produce a first formulation of a liquid solution;
   b. applying said first formulation of a liquid solution to the foliage of the plant, in an early stage of the plant's development, in an amount effective to inhibit rank growth of the plant without inducing Cut-Out;
   c. mixing together chlorocholine chloride, poly[oxyethylene(dimethyliminio)ethylene (dimethyliminio)ethylene]dichloride, choline chloride, and an inert carrier, to produce a second formulation of a liquid solution; and,
   d. applying said second formulation of a liquid solution to the foliage of the plant, in a late stage of the plant's development, in an amount effective to induce Cut-Out.

18. A method as in claim 17, in which said first formulation of a liquid solution has a lesser amount per weight of chlorocholine chloride than said second formulation.

19. A method as in claim 17 in which the amount of chlorocholine chloride applied to the plant in step b is less than the amount of chlorocholine chloride applied to the plant in step d.

20. A method as in claim 17 in which said early stage of development is approximately 10 to 20 weeks before harvest and said late stage of development is approximately 2 to 9 weeks before harvest.

* * * * *